United States Patent [19]

Morse et al.

[11] Patent Number: 5,196,581
[45] Date of Patent: Mar. 23, 1993

[54] ALKYLCARBAMOYLBORANE CYCLIC DIMERS

[75] Inventors: Karen W. Morse, Providence; Mohammad-Reza M.-D. Charandabi, Salt Lake City, both of Utah; Debra A. Feakes, Los Angeles, Calif.; Mallaiah Mittakanti, Logan, Utah

[73] Assignee: Utah State University Foundation, Logan, Utah

[21] Appl. No.: 694,320

[22] Filed: May 1, 1991

[51] Int. Cl.$^5$ .................................. C07F 5/02
[52] U.S. Cl. ............................ 564/8; 562/624
[58] Field of Search ........................ 564/8, 624

[56] References Cited

U.S. PATENT DOCUMENTS

| | | | |
|---|---|---|---|
| 4,312,989 | 1/1982 | Spielvogel et al. | 546/13 |
| 4,368,194 | 1/1983 | Spielvogel et al. | 424/185 |
| 4,587,359 | 5/1986 | Spielvogel et al. | 564/8 |
| 4,855,493 | 8/1989 | Spielvogel et al. | 561/575 |

*Primary Examiner*—Richard L. Raymond
*Attorney, Agent, or Firm*—Jon C. Christiansen

[57] ABSTRACT

Alkylcarbamoylborane cyclic dimers are synthesized through reactions of alkylcarbamoylborane adducts of amines. The inventive dimers have utility as reactants in the direct synthesis of alkylcarbamoylborane adducts of primary and secondary amines. Alkylcarbamoylborane adducts of primary and secondary amines and certain of the inventive dimers have biological activity as anti-tumor, hypocholesteremic, and anti-inflammatory agents. The cyclic dimers of this invention have the formula $[BHRC(O)NHR']_2$, examples of which include:

$[BH_2C(O)NHC_2H_5]_2$ $[BH_2C(O)NHCH_3]_2$ $[BH_2C(O)NHCH_2CH_2CH_3]_2$ $[BH_2C(O)NHCH_2CH=CH_2]_2$.

$[BH_2C(O)NHC(CH_3)_2]_2$.

$[BH(CH(CH_3)CH_2CH_3)C(O)NHCH_2CH_3]_2$.

7 Claims, No Drawings

ALKYLCARBAMOYLBORANE CYCLIC DIMERS

I. INTRODUCTION

This invention relates to the synthesis of alkylcarbamoylborane cyclic dimers. The invention includes methods for synthesizing the dimers, several formulations of the dimers, and a method for using the dimers as reactants in the synthesis of additional useful compounds.

Carbamoylborane adducts of amines, which are boron analogues of alpha amino acids, have received considerable interest recently because of their biological activity as anti-tumor, anti-inflammatory, and hypocholesteremic agents. Various examples of these compounds have been synthesized previously. However, current techniques do not allow the direct synthesis of carbamoylborane adducts of primary and secondary amines from their nitrilium salts.

Use of the alkylcarbamoylborane cyclic dimers described herein as reactants makes possible the direct and easy synthesis of carbamoylborane adducts of primary and secondary amines. In addition to having utility as reactants in the direct synthesis of biologically active compounds, it is expected that these dimers will themselves be valuable as biologically active agents. The N-ethylcarbamoylborane cyclic dimer exhibits hypocholesteremic effects, significantly reducing both serum cholesterol and triglycerides.

Direct synthesis of alkylcarbamoylborane adducts of amines is not possible using existing methods of synthesis. The number of substituent groups which can be included is limited; furthermore, in the exchange reactions used for synthesis of the primary and secondary amine derivatives, there is a tendency for the synthesis reactions to reach an equilibrium state, resulting in incomplete reaction and necessitating the separation of amine adducts from other components of the reaction.

One objective of this invention is to provide a method for synthesizing alkylcarbamoylborane cyclic dimers.

Another objective of this invention is to show the utilization of dimers as reactants in the direct and easy synthesis of alkylcarbamoylborane adducts of primary and secondary amines.

Another objective of this invention is to provide a new class of biologically active compounds.

The objectives, advantages and other aspects of the invention will be described more fully below.

II. SUMMARY OF INVENTION

Alkylcarbamoylborane cyclic dimers are synthesized from alkylcarbamoylborane adducts of tertiary amines. The invention includes methods for the synthesis of the inventive dimers as well as for the use of the dimers as reactants in the synthesis of alkylcarbamoylborane adducts of primary and secondary amines. Alkylcarbamoylborane adducts of primary and secondary amines, as well as certain of the inventive dimers, have biological activity as anti-tumor, hypocholesteremic, and anti-inflammatory agents. The general formula for the cyclic dimers is [BHRC(O)NHR']$_2$. Specific examples of the dimers include the following:

[BH$_2$C(O)NHC$_2$H$_5$]$_2$

[BH$_2$C(O)NHCH$_3$]$_2$

[BH$_2$C(O)NHCH$_2$CH$_2$CH$_3$]$_2$

[BH$_2$C(O)NHCH$_2$CH=CH$_2$]$_2$.

[BH$_2$C(O)NHC(CH$_3$)$_3$]$_2$.

[BH(CH(CH$_3$)CH$_2$CH$_3$)C(O)NHCH$_2$CH$_3$]$_2$.

III. DETAILED DESCRIPTION OF INVENTION

Several amine-boranes have been patented (U.S. Pat. No. 4,312,989, Spielvogel et al.; U.S. Pat. No. 4,368,194, Spielvogel et al.; U.S. Pat. No. 4,587,359, Spielvogel et al.; U.S. Pat. No. 4,855,493, Spielvogel et al.). Many types of aminomethylphosphonates, of the general form (RO)$_2$P(O)CHR'NR''$_2$, can be prepared through known synthetic methods. Examples of carbamoylborane adducts of some amines which have been synthesized using known methods are shown in Table I below. There have been no synthetic methods developed to form alkylcarbamoylborane adducts of amines, directly and cleanly, if any of the following substituent groups are present in the alkylamine cyanoborane: (1) primary amines, (2) secondary amines, and (3) amines containing substituent groups which react with triethyloxoniumtetrafluoroborate, sodium hydroxide, or water.

Table I

H$_3$N:BH$_2$CONHEt

H$_2$(CH$_3$)N:BH$_2$CONHEt

H(CH$_3$)$_2$N:BH$_2$CONHEt (CH$_3$)$_3$N: BH$_2$CONHEt

[CH$_2$N(CH$_3$)$_2$:BH$_2$CONHEt]$_2$

PH$_3$P:BH$_2$CONHEt

C$_5$H$_5$N:BH$_2$CONHEt (EtO)$_2$P(O)CH$_2$N(CH$_3$)$_2$:BH$_2$CONHEt

Currently used methods for synthesizing alkylcarbamoylborane adducts of amines also place substantial limitations on the functional groups which may be included in the product of the reaction. An additional problem with existing synthesis methods is the tendency for the reactions to reach an equilibrium state, rather than going to completion. Therefore, mixtures of both amines and amine adducts ar obtained and the individual components must be separated.

The novel carbamoylborane dimer described herein eliminates the need for two amines in the base exchange reactions, and thus, any equilibrium situation, and is ideally suited for the synthesis of N—H containing amine alkylcarbamoylboranes.

Reaction of the N-ethylcarbamoylborane adduct of diethyl-1-(dimethylamino)-methylphosphonate, (C$_2$H$_5$O)P(O)CH$_2$N(CH$_3$)$_2$BH$_2$C(O)NHC$_2$H$_5$, with a silica gel column resulted in the first example of a carbamoylborane cyclic dimer, [BH$_2$C(O)NHC$_2$H$_5$]$_2$, which is a carbamoyl analogue of the cyanoborane oligomer, [BH$_2$CN]$_x$. The dimer has been characterized by spectroscopic methods and elemental analysis. The dimer permits direct synthesis of N-ethylcarbamoylborane adducts of N—H containing amines via direct reaction. The method for synthesizing the N-ethylcarbamoylborane dimer, as well as related dimers, has been investigated, and several alternative synthetic methods have been developed. A description of methods for synthesis and identification of the dimers follows.

EXPERIMENTAL

Materials: All glass equipment was dried in an oven at 110 °C. and assembled under a stream of dry nitrogen. All reactions were carried out under an inert atmosphere. Silica gels, Kieselgel 60 (230–400 mesh) and 60 A (70–230 mesh), were used as received from E. M. Science and Aldrich, respectively. Solvents were dried and distilled prior to use. The N-ethylcarbamoylborane adduct of diethyl-1-(dimethylamino)-methylphosphonate was prepared as previously described.

Instrumental: $^1$H and $\{^1H\}^{13}$C NMR spectra were recorded in CDCl$_3$ using TMS as the internal standard on a Varian XL-300 spectrometer operating at 300 MHz and 75.44 MHz respectively or on a JEOL FX-90Q operating at 90 MHz and 22.63 MHz respectively. The $^{11}$B NMR spectra were recorded on a JEOL FX-90Q spectrometer operating at 28.69 MHz with chemical shifts reported relative to external BF$_3$OEt$_2$. Infrared spectra were obtained on a Perkin-Elmer 1750 FT spectrometer. The elemental analysis was perform by M-H-W Laboratories, Phoenix, Ariz.

SYNTHESIS OF ALKYLCARBAMOYLBORANE DIMERS: SPECIFIC EXAMPLES

In the following examples, the N-ethylcarbamoylborane cyclic dimer ( [BH$_2$C(O)NHC$_2$H$_5$]$_2$) was synthesized. Dimers containing alkyl groups other than ethyl can also be synthesized using the same synthetic procedure, provided a carbamoylborane starting material which contains the appropriate alkyl group is used. A list of possible alternative alkyl groups follows the descriptions of the synthetic methods.

Method 1: A flash chromatography column equipped with a flow controller valve was packed with Kieselgel 60. The N-ethylcarbamoylborane adduct of diethyl-1-(N,N-dimethylamino)-methylphosphonate was applied to the column as a 20% solution in the eluant (dichloromethane/ether, 70:30). Several fractions, 20 ×10 ml were collected and the components were identified using thin layer chromatography (TLC). The pure cyclic dimer was usually found in fractions 7–11. The solvent was removed at reduced pressure from these fractions and the resulting pure white solid was dried under vacuum. Yield of the dimer was 44% based on the amount of carbamoylborane adduct placed on the column.

Method 2: The N-ethylcarbamoylborane adduct of N-methylmorpholine was synthesized in a procedure analogous to the synthesis of the N-ethylcarbamoylborane adduct of pyridine. The adduct was heated at 60°–70 ° C. for 3 hours. The adduct was then dissolved in a minimal amount of the eluting solvent (dichloromethane/ether, 70:30) and applied to a short-path silica gel column. The 4×5 cm column was prepared with 60 A (70–230 mesh) silica gel according to the method of Harwood (Aldrichimica Acta 1985, 18(1)). Several fractions, 8×20 ml, were collected and the solvent was removed at reduced pressure. The crude product was recrystallized in ether/hexane and dried under vacuum. The pure cyclic dimer was obtained in 20% yield.

Method 3: The N-ethylcarbamoylborane adduct of N-methylmorpholine was placed in a Schlenk flask equipped with a cold finger and placed under high vacuum. The flask was slowly heated to a temperature of 65°–70 ° C. and kept at that temperature for a period of 3 hours. The resulting solid was stirred in dichloromethane, the solution filtered, and the solvent removed under reduced pressure. The dimer was recrystallized from dichloromethane/hexane. After the purified dimer was vacuum dried, the yield was calculated to be 20%.

Method 4: The N-ethylcarbamoylborane adduct of N-methylmorpholine was heated at 70°–80° C. for 3 hours. The adduct was then dissolved in a minimal amount of the eluting solvent (dichloromethane) and applied to a short-path reversed-phase silica gel column. The reversed phase silica packing material was prepared by allowing 300 ml of hexamethyldisilazane to react with a slurry of 300 g 60 A (70–230 mesh) silica gel and carbon tetrachloride for a period of 24 hours. After a fraction containing the volume of the column was eluted, the column was eluted with methanol until no residue was observed using TLC. This solution contained the initial starting material, the carbamoylborane dimer product, and free N-methylmorpholine which were then separated on a normal phase silica gel column. The dimer was recrystallized and dried under vacuum. The yield of the ethylcarbamoylborane dimer was 54% and the yields of the other dimers range from 20–50%.

Method 5: The N-ethylcarbamoylborane adduct of N-methylmorpholine was heated at 70°–80 ° C. for 3 hours. The adduct was then dissolved in a minimal amount of the eluting solvent (dichloromethane) and applied to a short-path acidic alumina column (Brockmann Activity I). After a fraction containing the volume of the column was eluted, the column was eluted with methanol until no residue was observed using TLC. This solution contained the initial starting material, the carbamoylborane dimer product, and free N-methylmorpholine which were then separated on a normal phase silica gel column. The dimer was recrystallized and dried under vacuum The yield of the dimer was 43%.

EXPERIMENTAL SUPPORT FOR FORMATION OF THE CARBAMOYLBORANE DIMER

The N—B bond cleavage which results in the decomposition of (C$_2$H$_5$O)$_2$P(O)CH$_2$N(CH$_3$)$_2$BH$_2$·C(O)NHC$_2$H$_5$ and the formation of an N-ethylcarbamoylbora cyclic dimer on the silica gel column can be attributed to the strong interaction of P=O with the silica gel and is supported by the fact that only P(V) fragments and no identifiable intact species can be isolated from the column materials. The structure of the cyclic dimer can be considered to be analogous to the cyanoborane oligomer which is formed from [BH$_3$CN]$^-$ in the presence of an acid.

Infrared, $^1$H NMR, $^{13}$C NMR, $^{11}$B NMR and mass spectral data support the proposed formulation for the cyclic dimer. The infrared spectrum (Table 1) exhibits absorptions characteristic of C=O, N-H, and B-H moieties. The assignments have been made based on the corresponding spectra of the cyanoborane cyclic oligomer ([BH$_2$CN]$_x$), the N-ethylcarbamoylborane adducts of several trialkylamines and the generally accepted assignments for organic amides. The B—H stretching mode of the N-ethylcarbamoylborane adduct of N-methylmorpholine is reported at 2369 cm$^{-1}$ which is consistent with solution spectra of other trialkylamine adducts. The shift to higher energy, 2400$^{-1}$, of the B—H stretching mode in the cyclic dimer is consistent with the change observed when the amine of the N-ethylcarbamoylborane is changed from a trialkylamine (2330 cm$^{-1}$) to a dialkylamine (2365 cm$^{-1}$); this may be attributed to analogous inductive effects occurring in the two systems. The N—H stretching mode in the N-methylmorpholine carbamoylborane adduct exhibits two bands which suggests some degree of intermolecular hydrogen bonding. However, the shift to higher frequency of the N—H stretching mode 3410 cm$^{-1}$ in the dimer ring suggests an absence of intermolecular hydrogen bonding.

In the N-methylmorpholine adduct the amide I and amide II bands are observed at 1595 and 1477 cm$^{-1}$ respectively, consistent with solution spectra obtained on other trialkylamine adducts. In contrast, the amide I and amide II bands of the dimer are observed at 1570 and 1520 cm$^{-1}$. The shift to higher wave number of the amide II band corresponds to the dimer structure in that the N—H bond length would be expected to decrease since the lone-pair on the amide is bonded to the boron. The shift to lower energy of the C=O mode implies a decrease in partial positive charge on the carbon and a lengthening of the carbon-oxygen bond resulting from the relative increase in electron density on the boron (and concurrent increase in the B—H frequency).

The $^{11}$B NMR for both the N-methylmorpholine adduct and the cyclic dimer correlate well with previously reported spectra. Each triplet indicates the presence of a BH: moiety (with comparable coupling constants (Table 1)) while the proton-decoupled spectra exhibit only a single resonance, indicating the presence of a single type of boron in each compound.

The $^1$H and {$^1$H} $^{13}$C NMR spectra of the N-methylmorpholine adduct show absorptions similar to those reported for other amine N-ethylcarbamoylboranes (e.g. pyridine and trimethylamine) with peaks attributable to the N-ethyl group and the N—H on the carbamoyl function. The N-ethyl resonances in the $^{13}$C NMR of the ring compound correspond to those observed for carbamoylborane adducts.

The mass spectral data for the ring compound, exhibiting no mass higher than 169, supports the assignment of a cyclic dimer structure rather than a linear oligomeric structure. The peak clusters and their relative intensities are what would be expected from the natural abundance of the boron isotopes.

A ring resulting from boron coordination to the carbonyl oxygen atom would be expected to have an IR absorption corresponding to the C=N$^4$R and also a uB NMR shift downfield of that observed. On this basis, the latter structure can be eliminated.

The reaction of the dimer with methylamine supports the ring formulation since no other product other than the known methylamine carbamoylborane is generated. Additionally, this result indicates that use of the rings offers potential for formation of a large number of primary and secondary amine carbamoylboranes at rates faster than reported exchange reactions. For example, exchange between methylamine and the carbamoylborane adduct of trimethylamine showed the reaction to be slower, being 65% complete in one week.

SYNTHESIS OF CARBAMOYLBORANE DIMERS: GENERAL CHARACTERISTICS

Column Parameters

Although heating of the alkycarbamoylborane adducts of amines increases the yield of the carbamoylborane dimers, using different column materials can change the yield of the dimer as well. Column materials which have been used to synthesize the dimers are: (1) silica gel, (2) reversed-phase silica gel, and (3) acidic alumina.

Anything that the dimer is soluble in (i.e. most organic solvents) can be used as an eluant. The methyl and ethylcarbamoylborane dimers are not soluble in hexane or in solvents which are less polar than hexane. The dimers containing larger substituent groups are also soluble in hexane and pentane. None of the dimers are soluble in water. The less polar solvents do not transport the dimers as rapidly as the polar solvents. Therefore, the more polar solvents, such as dichloromethane, are more time efficient.

Heating Procedure

The dimer does not form spontaneously at room temperature. Heating the N-methylmorpholine adducts between 40° C. and approximately 100° C. (decomposition point) followed by elution through a column results in dimer formation. As the temperature is decreased, the length of heating is increased. However, any heating at all appears to increase the yield of the dimer. The most important factor is the heating procedure.

Choice of Amine Base

Various amine base carbamoylborane adducts have been used in dimer preparation, including the adducts of trimethylamine, pyridine, and N-cyclohexylmorpholine. Carbamoylborane adducts of diethyl 1-(N,N-dimethylamino)-methylphosphonate and N-methylmorpholine proved to be better reaction substrates, and hence were used in the examples shown above.

Alternate Synthesis of the Dimers

No other technique has worked as efficiently as the columns. Heating the N-methylmorpholine adduct under vacuum yields the dimers in approximately 20% yield. Heating the N-methylmorpholine adducts in hexane yields decomposition products, but no dimer products.

GENERAL FORMULA

The general formula for the compounds which can be synthesized is [BHRCONHR']$_2$. Attempts to synthesize N-methylmorpholine adducts with R' groups which are stable cations (for example, isopropyl or hydrogen) have proven unsuccessful. Additionally, the benzyl group has not been successfully incorporated into the structures. The structures which have been successfully synthesized include the following R and R' groups:

R = H and
R' = —CH$_3$, —CH$_2$CH$_3$, —CH$_2$CH$_2$CH$_3$, —CH$_2$CH=CH$_2$, or —C(CH$_3$)$_3$ OR
R = —CH(CH$_3$)CH$_2$CH$_3$ and R' = —CH$_2$CH$_3$

FORMATION OF A CARBAMOYLBORANE ADDUCT OF A PRIMARY AMINE

The N-ethylcarbamoylborane cyclic dimer (0.0765 g. 0.425 mmol) was placed in a medium wall NMR tube equipped with a 10/30 standard taper joint and an excess of anhydrous methylamine was vapor transferred into the apparatus. After several freeze/thaw cycles, the NMR tube was flame-sealed and slowly warmed to ambient temperature. The progress of the reaction was monitored by $^{11}$B NMR. After one week the reaction was shown to be 81% complete by $^{11}$B NMR. The reaction was complete in two weeks. Spectral analysis of the product agrees with published values for the reaction of methylamine with the ethylcarbamoylborane adduct of trimethylamine.

The dimers have also been allowed to react with monomethylamine, dimethylamine, trimethylamine and diisopropyl(N-methylamino)methylphosphonate to form their corresponding amine-carbamoylborane adducts.

BIOLOGICAL ACTIVITY OF BORON ANALOGUES OF ALPHA AMINO ACIDS

Interest in the boron analogues of alpha amino acids stems from their biological activity as anti-tumor, hypocholesteremic, and anti-inflammatory agents (see J. Pharm Sci. vol. 69, p. 1025, 1979; vol. 69, p. 1025, 1980; vol. 70, p. 339, 1981). To date, preliminary studies indicate that many of these boron containing compounds reduce cholesterol levels (both serum triglyceride and serum cholesterol) to the same degree as, if not better than, a currently available medication, clofibrate, as shown in Table II (see J. Am. Chem. Soc., vol. 94, p. 8597, 1972; J. Organomet. Chem., vol. 17, p. 255, 1983).

TABLE II

|  | % Cholesterol Reduction | % Triglyceride Reduction |
| --- | --- | --- |
| clofibrate | 13 | 25 |
| $(CH_3)_3N:BH_3$ | 30 | 15 |
| $(CH_3)_3N:BH_2CN$ | 28 | 42 |
| $(CH_3)_3N:BH_2COOH$ | 49 | 39 |
| $(CH_3)_3N:BH_2CONHEt$ | 42 | 36 |

Preliminary data also suggest that the presence of an amine hydrogen may enhance the biological activity of the boron adducts (see J. Am. Chem. Soc., vol. 94, p. 8597, 1972). For this reason, it is of particular significance that the cyclic dimer described here can be used as a reactant in the synthesis of carbamoylborane adducts of primary and secondary amines. As shown in Table III below, monomethylamine carboxyborane has a greater activity at lowering serum triglyceride levels than its tertiary amine counterpart, trimethylamine carboxyborane. Both the ethylcarbamoylborane adducts of ammonia and dimethylamine have a greater effect at lowering serum cholesterol and serum triglyceride, respectively, than trimethylamine ethylcarbamoylborane.

TABLE III

| NH CONTAINING AMINE COMPOUND | TERTIARY AMINE COMPOUND | BIOLOGICAL ACTION |
| --- | --- | --- |
| $(CH_3)H_2N:BH_2COOH >$ | $(CH_3)_3N:BH_2COOH$ | B |
| $H_3N:BH_2CONHEt >$ | $(CH_3)_3N:BH_2CONHEt$ | A |
| $(CH_3)_2HN:BH_2CONHEt >$ | $(CH_3)_3N:BH_2CONHEt$ | B |

Hypocholesteremic Activity:
A) serum cholesterol lowering
B) serum triglyceride lowering

BIOLOGICAL ACTIVITY OF ALKYCARBAMOYLBORANE CYCLIC DIMERS

The ethylcarbamoylborane dimer had significant ability to reduce both serum triglyceride and serum cholesterol levels. Serum cholesterol was lowered by 34% on day 16 and serum triglycerides were lowered by 43% (unpublished results). Since no other dimeric species of this type have been reported, the extent of the structure/activity relationships of this class of compounds have not been explored.

The foregoing description of this invention so fully reveals the general nature of this invention that others can, by applying current knowledge, readily modify such description and/or adapt it for various applications without departing from the generic concept, and therefore, such adaptations and modifications should and are intended to be comprehended within the meaning and range of equivalents of the following claims, which claims define subject matter regarded to be our invention.

We claim:

1. An alkylcarbamoylborane cyclic dimer comprising $[BH_2C(O)NHR']_2$; wherein R' is selected from the group consisting of $-CH_3$, $-CH_2CH_3$, $-CH_2CH_2CH_3$, $-CH_2CH=CH_2$, and $-C(CH_3)_3$.

2. A cyclic dimer in accordance with claim 1 wherein said dimer is $[BH_2C(O)NHC_2H_5]_2$.

3. A cyclic dimer in accordance with claim 1 wherein said dimer is $[BH_2C(O)NHCH_3]_2$.

4. A cyclid dimer in accordance with claim 1 wherein said dimer is $[BH_2C(O)NHCH_2CH_2CH_3]_2$.

5. A cyclid dimer in accordance with claim 1 wherein said dimer is $[BH_2C(O)NHCH_2CH=CH_2]_2$.

6. A cyclid dimer in accordance with claim 1 wherein said dimer is $[BH_2C(O)NHC(CH_3)_3]_2$.

7. An alkylcarbamoylborane cyclic dimer comprising $[BH(CH(CH_3CH_2CH_3)C(O)NHCH_2CH_3]_2$.

* * * * *

UNITED STATES PATENT AND TRADEMARK OFFICE
CERTIFICATE OF CORRECTION

PATENT NO. : 5,196,581
DATED : March 23, 1993
INVENTOR(S) : Utah State University Foundation It is certified that error appears in the above-indentified patent and that said Letters Patent is hereby corrected as shown below:

Column 5, line 27, "BH:" should be "$BH_2$".

Column 8, line 50, "$[BH(CH(CH_3CH_2...$" should be "$[BH(CH(CH_3)CH_2...$"

Signed and Sealed this

Twenty-third Day of November, 1993

BRUCE LEHMAN

*Attest:*

*Attesting Officer*     Commissioner of Patents and Trademarks